US012694520B2

(12) United States Patent
Kaeseberg

(10) Patent No.: US 12,694,520 B2
(45) Date of Patent: Jul. 28, 2026

(54) MEDICAL IMAGE DATA PROCESSING TECHNIQUE

(71) Applicant: Stryker European Operations Limited, Carrigtwohill (IE)

(72) Inventor: Marc Kaeseberg, Biesenthal (DE)

(73) Assignee: Stryker European Operations Limited, Carrigtwohill (IE)

( * ) Notice: Subject to any disclaimer, the term of this patent is extended or adjusted under 35 U.S.C. 154(b) by 309 days.

(21) Appl. No.: 18/372,891

(22) Filed: Sep. 26, 2023

(65) Prior Publication Data

US 2024/0112331 A1    Apr. 4, 2024

(30) Foreign Application Priority Data

Sep. 30, 2022    (EP) ..................................... 22198927

(51) Int. Cl.
| | |
|---|---|
| *G06K 9/00* | (2022.01) |
| *G06T 5/40* | (2006.01) |
| *G06T 7/00* | (2017.01) |
| *G06V 10/24* | (2022.01) |
| *G06V 10/25* | (2022.01) |
| *G16H 30/20* | (2018.01) |
| *G16H 30/40* | (2018.01) |

(52) U.S. Cl.
CPC .............. *G06T 7/0012* (2013.01); *G06T 5/40* (2013.01); *G06V 10/24* (2022.01); *G06V 10/25* (2022.01); *G16H 30/20* (2018.01); *G16H 30/40* (2018.01); *G06T 2207/30008* (2013.01)

(58) Field of Classification Search
None
See application file for complete search history.

(56) References Cited

U.S. PATENT DOCUMENTS

| | | | |
|---|---|---|---|
| 6,560,354 | B1 | 5/2003 | Maurer, Jr. et al. |
| 7,194,295 | B2 | 3/2007 | Vilsmeier |
| 10,403,009 | B2 | 9/2019 | Mariampillai et al. |
| 10,470,825 | B2 | 11/2019 | Gallop et al. |

(Continued)

FOREIGN PATENT DOCUMENTS

| | | |
|---|---|---|
| CA | 2776952 A1 | 4/2011 |
| EP | 3493161 A2 | 6/2019 |

(Continued)

OTHER PUBLICATIONS

Xu, Yao et al., "Advances on Pancreas Segmentation: A Review", Multimedia Tools and Applications, vol. 76, 2020, pp. 6799-6821.

(Continued)

*Primary Examiner* — Wei Wen Yang
(74) *Attorney, Agent, or Firm* — Howard & Howard Attorneys PLLC

(57) ABSTRACT

A method for processing medical image data of a patient's body. The method includes obtaining medical image data of a patient's body, identifying a first portion of the medical image data that represents at least one predefined anatomical region of the patient's body, and determining, based on the first portion of the medical image data, a first criterion for allocating pixels or voxels of the medical image data to a first surface represented by the medical image data. A computing system, a computer program, and a carrier containing the computer program is also disclosed.

16 Claims, 9 Drawing Sheets

(56) References Cited

U.S. PATENT DOCUMENTS

| | | |
|---|---|---|
| 2011/0002523 A1 | 1/2011 | Prakash et al. |
| 2014/0316234 A1 | 10/2014 | Waite et al. |
| 2018/0046875 A1 | 2/2018 | Caluser |
| 2019/0231433 A1 | 8/2019 | Amanatullah |
| 2019/0232143 A1 | 8/2019 | Mac Donald et al. |
| 2020/0001589 A1 | 1/2020 | Brandt et al. |
| 2020/0015895 A1 | 1/2020 | Frielinghaus et al. |
| 2021/0158511 A1* | 5/2021 | Guo ........................ G16H 50/30 |
| 2022/0039868 A1* | 2/2022 | Chaoui .................. G06N 3/084 |

FOREIGN PATENT DOCUMENTS

| | | |
|---|---|---|
| WO | 2017190210 A1 | 11/2017 |
| WO | 2018162079 A1 | 9/2018 |
| WO | 2021030629 A1 | 2/2021 |

OTHER PUBLICATIONS

Xu, Yao et al., "Advances on Pancreas Segmentation: A Review", Multimedia Tools and Applications, vol. 79, 2020, pp. 6799-6821.

* cited by examiner

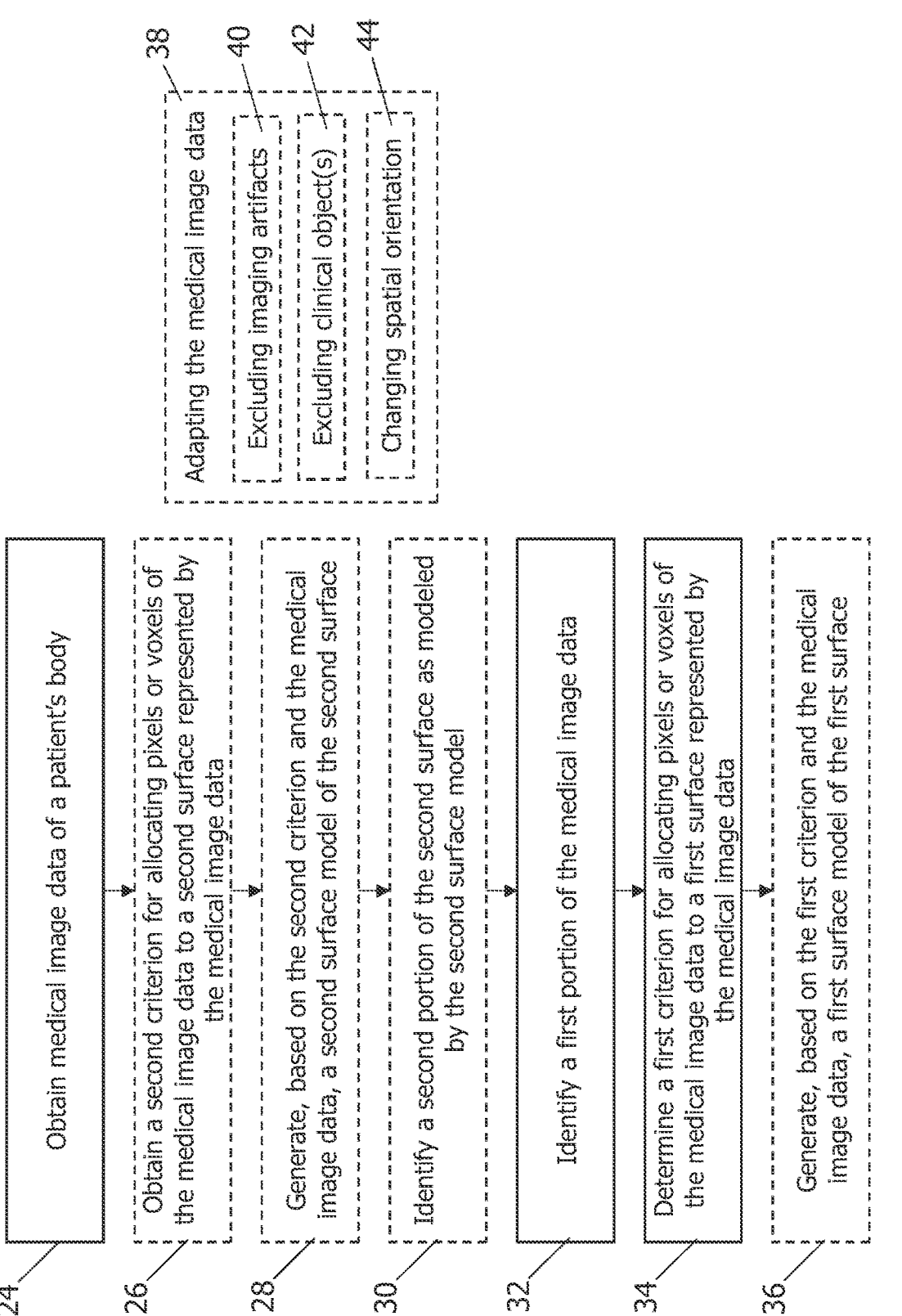

Obtain medical image data of a patient's body

Obtain a second criterion for allocating pixels or voxels of the medical image data to a second surface represented by the medical image data Generate, based on the second criterion and the medical image data, a second surface model of the second surface Identify a second portion of the second surface as modeled by the second surface model Identify a first portion of the medical image data Determine a first criterion for allocating pixels or voxels of the medical image data to a first surface represented by the medical image data Generate, based on the first criterion and the medical image data, a first surface model of the first surface Adapting the medical image data Excluding imaging artifacts Excluding clinical object(s)

Changing spatial orientation

Fig. 2

MEDICAL IMAGE DATA PROCESSING TECHNIQUE

PRIORITY CLAIM

This application claims priority under 35 U.S.C. § 119 to European Patent Application No. 22198927.0, filed Sep. 30, 2022, the entire contents of which are hereby incorporated by reference.

TECHNICAL FIELD

The present disclosure generally relates to processing medical image data. A method for processing medical image data of a patient's body, a computing system, a is computer program and a carrier are disclosed.

BACKGROUND

Medical image data such as computed tomography, CT, image data, magnetic resonance, MR, image data and x-ray image data is often used for diagnostic purposes, surgical planning or surgical navigation.

In certain scenarios, surfaces represented by the medical image data are of interest for the clinical personnel or for subsequent software-based data processing techniques. Such surfaces may include a bone surface of a patient's body, a skin surface of the patient's body and a surface of a clinical object such as an eye protection, a head support or an implant. A visualization of the respective surfaces may be provided to the clinical personnel for diagnostic or planning purposes, or during surgical navigation. Software-based data processing techniques such as surface-based image registration techniques may rely on the respective surfaces obtained from the medical image data.

SUMMARY

There is a need for a technique that allows for an accurate detection of a surface represented by medical image data.

According to a first aspect, a method for processing medical image data of a patient's body is provided. The method comprises (a) obtaining medical image data of a patient's body, (b) identifying a first portion of the medical image data that represents at least one predefined anatomical region of the patient's body, and (c) determining, based on the first portion of the medical image data, a first criterion for allocating pixels or voxels of the medical image data to a first (e.g., refined, fine or accurate) surface represented by the medical image data. The first criterion may be specific (e.g., unique) for the first portion. The first criterion may be patient-specific.

The medical image data may comprise at least one of two-dimensional and three-dimensional image data. The medical image data may comprise one or more images of the patient's body. The first portion of the medical image data may be consist of a subset of pixels or voxels of the medical image data. The predefined anatomical region may comprise one or more anatomical landmarks and, optionally, an area having a predefined form (e.g., at least one of a predefined size and a predefined shape) and having a predefined spatial relationship to the one or more anatomical landmarks.

The first criterion may comprise a (e.g., threshold) value of pixels or voxels of the medical image data representing a part of the first surface.

The value may be representative of a strength of a signal received by a detector of a medical imaging device. The value may correspond to an intensity value, for example in Hounsfield units.

The method may further comprise generating, based on the first criterion and the medical image data, a first (e.g., refined, fine or accurate) surface model of the first (e.g., refined, fine or accurate) surface. The first surface model may be generated by including all pixels or voxels of (e.g., the first portion of) the medical image data in the first surface model. Generating the first surface model may comprise generating a rendering of the first surface using the first criterion.

The method may further comprise obtaining a (e.g., determined, predefined or user-defined) second criterion for allocating pixels or voxels of the medical image data to a second surface represented by the medical image data. The method may comprise generating, based on the second criterion and the medical image data, a second (e.g., preliminary or rough) surface model of the (e.g., preliminary or rough) second surface. The method may further comprise identifying a second portion of the second surface as modeled by the second surface model that represents the at least one predefined anatomical region.

The first portion of the medical image data may be identified based on the second portion. For example, all images or voxels associated with the second portion may be associated to the first portion. Alternatively, or in addition, the first criterion may be (e.g., locally) determined based on the second portion.

The first criterion (e.g., a threshold value or a range of pixel or voxel values) may be determined based on a (e.g., intensity) value of at least one pixel or voxel of the first portion of the medical image data. Determining the first criterion may comprise selecting the value of the at least one pixel or voxel as the first criterion.

The first criterion may be determined based on values of pixels or voxels of one or more sets of pixels or voxels of the medical image data. The pixels or voxels of each set may lie along a same straight line associated with the respective set. Determining the first criterion may comprise selecting the value of one of the sets of pixels or voxels as the first criterion, or averaging a selection of values of the pixels or voxels to obtain the first criterion.

The line may have a predefined spatial relationship to the second surface as modeled by the second surface model. The line may have a predefined length.

At least one of the following conditions may be fulfilled: the line intersects the second portion; the line has a predefined angle relative to at least a part of the second portion; the line intersects the second portion at an intersection point and is orthogonal to the second portion at the intersection point; the line has a predefined angle relative to another line associated with another one of the one or more sets; the line has a predefined distance relative to another line associated with another one of the one or more sets.

The first criterion may be determined based on a trained machine learning model and/or a gradient analysis of pixels or voxels of at least one of the sets.

The second criterion may be determined based on the medical image data. Optionally, the second criterion may be determined by or based on at least one of:

(i) a histogram analysis of values of pixels or voxels of the medical image data; and (ii) a trained machine learning model.

Multiple first portions of the medical image data may be identified (e.g., in step (b) or by repeating step (b)). Multiple first criteria may be determined (e.g., in step (c) or by repeating step (c)) based on the multiple first portions for allocating pixels or voxels of the medical image data to respective first surfaces represented by the medical image data.

The method may further comprise adapting the medical image data before performing at least one of the method steps, wherein, during the at least one method step, the adapted medical image data is used instead of the medical image data. Adapting the medical image data comprises at least one adaption selected from: (i) excluding imaging artifacts from the medical image data; (ii) excluding one or more clinical objects represented by the medical image data; and (iii) changing a spatial orientation of the medical image data.

Adapting the medical image data may comprise (i) performing, iteratively, two or more of the at least one adaption, or (ii) performing, iteratively, one of the at least one adaption multiple times, to gradually adapt the medical image data.

The medical image data may be adapted according to the method of the second aspect.

Each surface may be of a surface type. The surface type may be one of (i) a bone surface of the patient's body, (ii) a skin surface of the patient's body, or (iii) a surface of a clinical object (e.g., a non-organic object, a non-anatomical object, a metal object, an eye protection, a head or patient support or an implant).

At least the step (c) may be performed multiple times, each time for a different surface type of the first surface.

According to a second aspect, a method for processing medical image data of a patient's body is provided. The method comprises obtaining medical image data of a patient's body. The method further comprises adapting the medical image, wherein adapting the medical image data comprises at least one adaption selected from: (i) excluding imaging artifacts from the medical image data; (ii) excluding one or more clinical objects represented by the medical image data; and (iii) changing a spatial orientation of the medical image data.

According to the second aspect, the medical image data may be iteratively adapted. This means that after an adaption, the adapted medical image data may be used for a subsequent adaption. After the subsequent adaption, the resultant medical image data may be used for a later adaption and so on. Adapting the medical image data may comprise (i) performing, iteratively, two or more of the at least one adaption, or (ii) performing, iteratively, one of the at least one adaption multiple times, to gradually adapt the medical image data.

Adapting the medical image data may comprise excluding imaging artifacts from the medical image data before changing a spatial orientation of the (e.g., adapted) medical image data.

Adapting the medical image data may comprise excluding imaging artifacts from the medical image data before excluding one or more clinical objects represented by the (e.g., adapted) medical image data.

Adapting the medical image data may comprise changing a spatial orientation of the medical image data before excluding one or more clinical objects represented by the (e.g., adapted) medical image data.

Adapting the medical image data may comprise excluding imaging artifacts from the medical image data, subsequently changing a spatial orientation of the (e.g., adapted) medical image data and subsequently excluding one or more clinical objects (e.g., one after another) represented by the (e.g., adapted) medical image data (e.g., having the changed spatial orientation).

The method may comprise determining a (e.g., the second) surface model based on the medical image data (e.g., based on the second criterion) without imaging artifacts (e.g., after having removed the imaging artifacts). The spatial orientation of the medical image data may be changed based on the determined surface model. A pose of a patient may be determined based on the (e.g., second) surface model and compared with a predefined pose. The spatial orientation of the image data may be adjusted such that the pose of the patient corresponds to the predefined pose.

The method may comprise detecting a predefined clinical object (e.g., an eye protection) based on the medical image data (e.g., without the imaging artifacts and/or with adjusted spatial orientation). The predefined clinical object may be excluded from the medical image data (e.g., without imaging artifacts and/or with the adjusted spatial orientation).

The method may comprise determining a (e.g., the second) surface model based on the (e.g., adapted) medical image data (e.g., based on the second criterion) after having excluded the predefined clinical object. Another clinical object (e.g., a head support or an implant) may then be excluded or removed from the (e.g., adapted) medical image data based on the determined surface model.

The adapted medical image data may be used to determine the first criterion as described for the method according to the first aspect, whereas the second criterion may be predefined or determined based on the raw medical data (e.g., the medical data before the adaption).

The method according to the second aspect may be combined with the method according to the first aspect, and vice versa. The "medical image data" as used in the method of the first aspect may correspond to the adapted medical image data obtained with the method according to the second aspect.

According to a third aspect, a computing system is provided. The computing system comprises at least one processor configured to carry out the method according to the first aspect or the second aspect. The computing system may further comprise a medical imaging device configured to generate the medical image data.

According to a fourth aspect, a computer program is provided. The computer program comprises instructions which, when executed on at least one processor, cause the at least one processor to carry out the method according to the first aspect or the second aspect.

According to a fifth aspect, a carrier is provided. The carrier contains the computer program of the fourth aspect. The carrier may be one of an electronic signal, an optical signal, a radio signal, or a (e.g., non-transitory) computer readable storage medium.

BRIEF DESCRIPTION OF THE DRAWINGS

Further details, advantages and aspects of the present disclosure will become apparent from the following embodiments taken in conjunction with the drawings, wherein:

FIG. 2 shows a method in accordance with the present disclosure;

DETAILED DESCRIPTION

Figure 1:
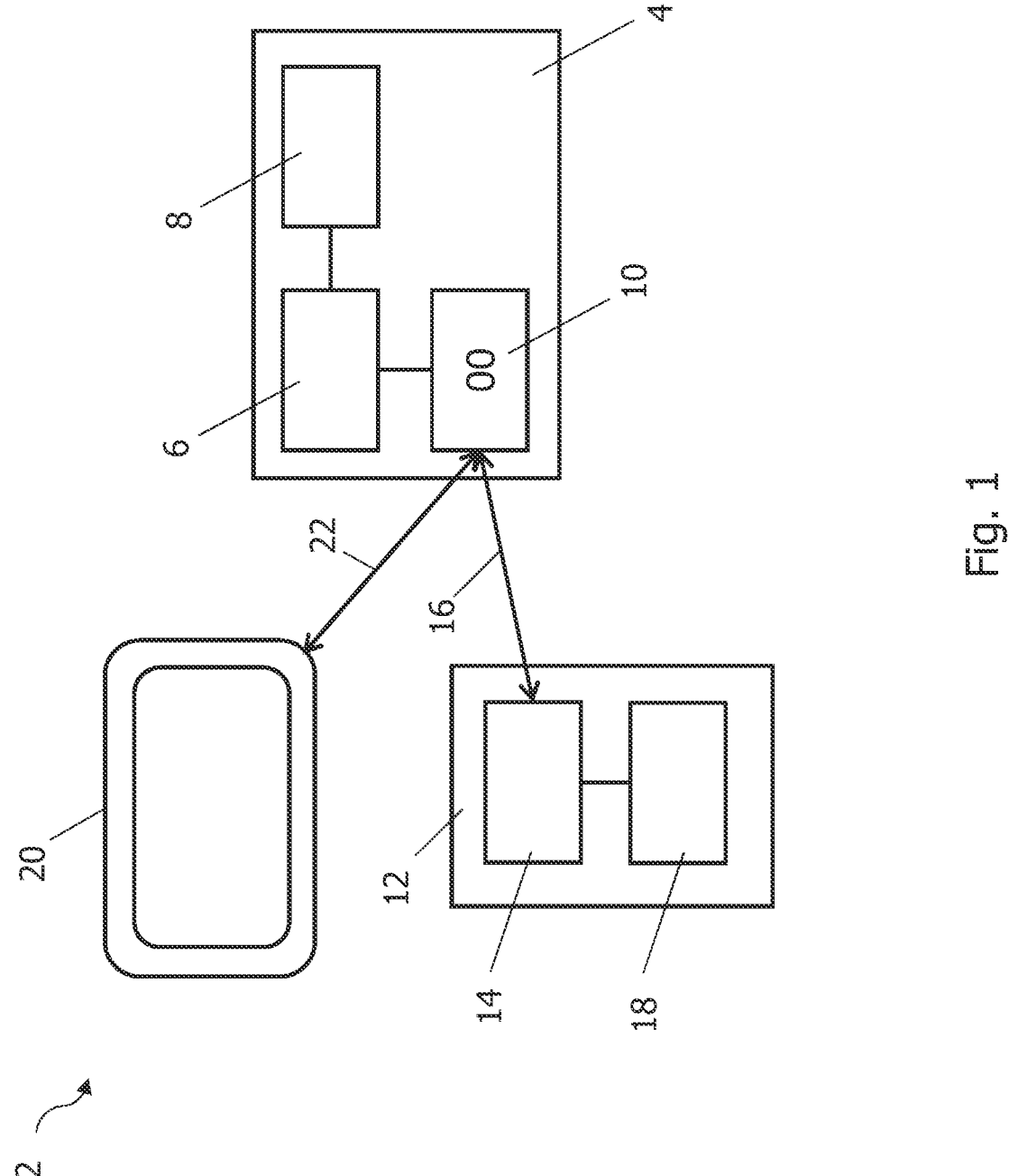
FIG. 1 shows a computing system in accordance with the present disclosure.

In the following description, exemplary embodiments of a surgical navigation system and a surgical navigation method will be explained with reference to the drawings. The same reference numerals will be used to denote the same or similar structural features.

FIG. 1 shows a first embodiment of a computing system 2 in accordance with the present disclosure. The computing system 2 comprises a processing unit 4 including at least one processor 6, at least one memory 8 and at least one interface 10. The processor 6 is communicatively coupled to the memory 8 and the interface 10. The memory 8 stores instructions which, when executed by the processor 6, configure the processor 6 to perform the method(s) described herein.

The computing system 2 may further comprise a medical imaging device 12, an interface 14 of which may be communicatively coupled to the interface 10, for example via a wired or wireless connection 16. The medical imaging device 12 comprises a detector 18 configured to receive a (e.g., radio frequency, RF, or x-ray) signal. The medical imaging device 12 is configured to generate medical image data based on the signal received by the detector 18. The medical imaging device 12 may be an x-ray imaging device, a (e.g., cone beam) computed tomography, CT, device, or a magnetic resonance, MR, imaging device. Other variants such as an ultrasonic imaging device are also possible. The medical imaging device 12 may be configured to transmit the generated medical image data to the processing unit 4 or to a storage unit (not shown) communicatively coupled to the processing unit 4.

The computing system 2 may further comprise a display device 20, which may be communicatively coupled to the interface 10, for example via a wired or wireless connection 22. The display device 20 may be a standalone display screen, a display of a surgical navigation system or an augmented reality, AR, device such as a head-mounted display, HMD. The display device 20 is configured to display a visualization based on instructions received from the processing unit 4.

FIG. 2 shows a method in accordance with the present disclosure. The method may be a computer-implemented method. The method can generally be referred to as a data processing method and does not comprise a surgical step. The method may be performed by the processing system 2, at least by the at least one processor 6 of the processing unit 4.

In step 24, medical image data of a patient's body is acquired. The medical image data may be or comprise two-dimensional image data and/or three-dimensional image data. The medical image data may comprise pixels representing at least one (e.g., two-dimensional) patient image. Alternatively, or in addition, the medical image data may comprise voxels representing at least one (e.g., exactly one) volumetric patient image. The medical image data may be or comprise CT image data, MR image data and/or x-ray image data. The medical image data may be representative of at least a part of the patient's body (e.g., a head of the patient). The medical image data may be acquired from the medical imaging device 12 or the storage unit.

In an optional step 26, a second criterion for allocating pixels or voxels of the medical image data to a second surface represented by the medical image data is obtained. This means that all pixels of voxels allocated or assigned to the second surface fulfil the second criterion. The "second criterion" may also be referred to as preliminary criterion, rough criterion or estimation criterion, and the "second surface" may also be referred to as preliminary surface, rough surface or estimated surface. The second criterion may comprise a (e.g., threshold) value or a range of values of pixels or voxels of the medical image data associated with the second surface. The value may be representative of a pixel or voxel intensity or, generally speaking, representative of a strength of a signal received by the detector 18 of the medical imaging device 12.

The second criterion may be predefined, user-defined or determined based on the medical image data. The second criterion may be (e.g., automatically) determined by or based on at least one of: (i) a histogram analysis of values of pixels or voxels of the medical image data; and (ii) a trained machine learning model.

Figure 3:
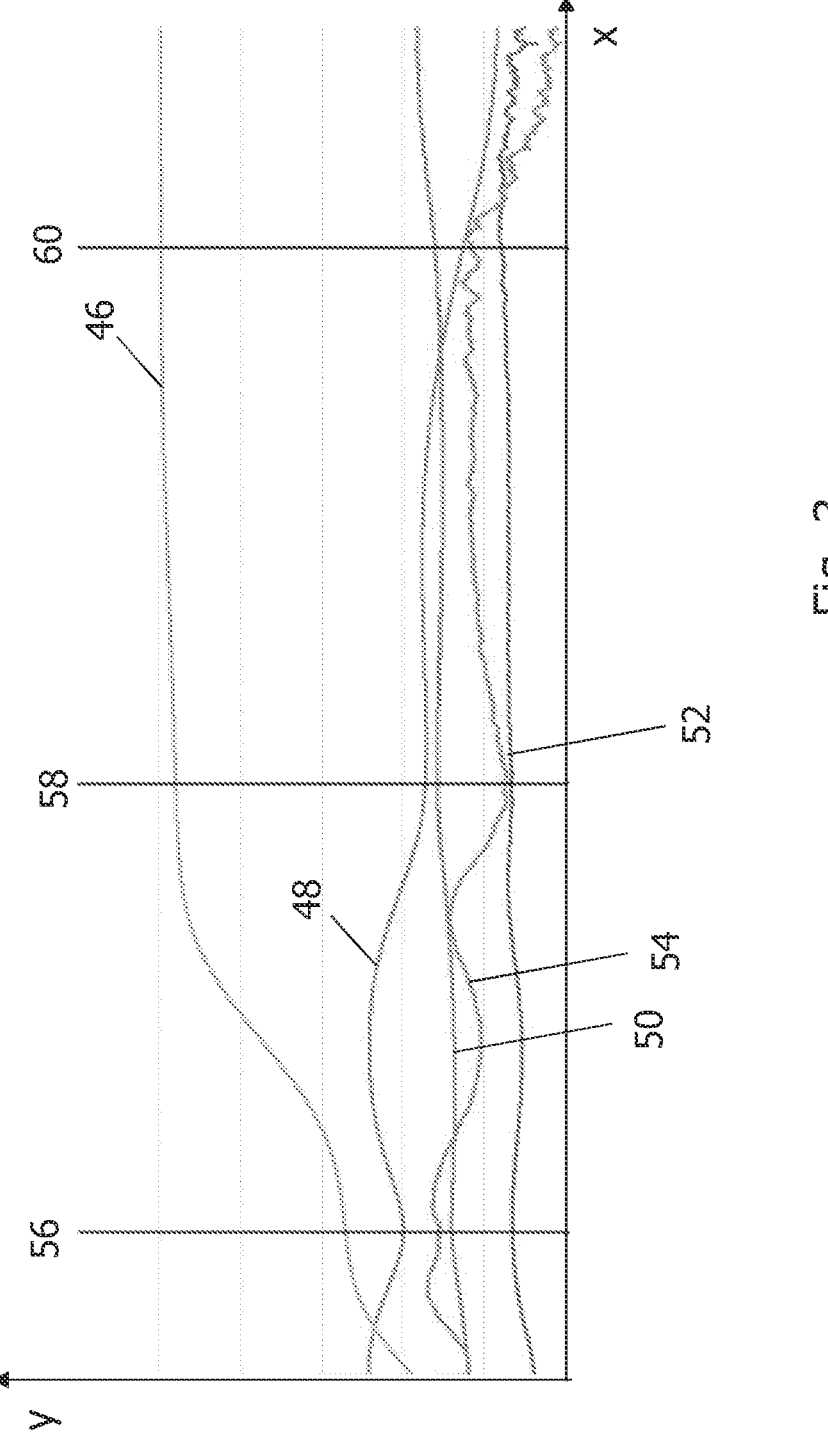
FIG. 3 shows exemplary histograms of medical image data in accordance with the present disclosure.

FIG. 3 shows exemplary histograms of medical image data in accordance with the present disclosure. In this example, the obtained medical image data is CT image data comprising a plurality of voxels, each having a certain value. The overall medical image data (e.g., all voxels comprised therein) can be analyzed using a histogram analysis or a machine learning model to obtain the second criterion.

Each of the curves 48-54 in FIG. 3 has been normalized to fit into a common diagram and a smoothing filter has been applied to each curve to remove noise. The curve 46 of FIG. 3 represents a sum histogram, which indicates, for different voxel (e.g., intensity) values x, the number of voxels y having voxel values lower than or equal to x. The curve 48 represents an intensity histogram, which indicates, for different voxel values of x, the number of voxels y having voxels values equal to x. The curve 50 represents a first gradient histogram which indicates, for different voxel values x, the sum y of gradients G of all voxels having voxel values equal to x. Each gradient G may be determined as $G=(g_a^2+gb^2+g_c^2)\hat{}0.5$, wherein $g_a$, $g_b$ and $g_c$ each designate a gradient g of the respective voxel in a first spatial dimension a, in a second spatial dimension b and in a third spatial dimension c. While the curve 50 may be generated based on gradients $g_a$, $g_b$ and $g_c$ determined using a 3×3×3 kernel (e.g., based on the voxel value of a respective voxel and two bounding voxels, adjacent to the respective voxel along the direction a, b or c), the curve 52 represents a second gradient histogram, wherein the gradients $g_a$, $g_b$ and $g_c$ may be determined using a 2×2×2 kernel (e.g., based on the voxel value of a respective voxel and one adjacent voxel following the respective voxel in the direction a, b or c). The curve 54 corresponds to a scaled proportion between the curves 50 and 52. One or more of the curves can be analyzed using various predefined thresholds, pattern recognition techniques or the like to identify the second criterion. Alternatively, or in addition, a trained machine learning model may use one or more of the curves or the overall medical image data as input and output the second criterion.

In the example of FIG. 3, the lines 56, 58 and 60 each indicate a threshold voxel value that can be used as the second criterion for a particular surface type. In particular, voxels of the medical image having a voxel value as indicated by the line 56 may be considered to be part of a skin surface represented by the medical image data, voxels of the medical image having a voxel value as indicated by the line 58 may be allocated to a bone surface represented by the medical image data and voxels of the medical image having a voxel value as indicated by the line 60 may be associated with a metal surface (e.g., of an eye protection, a head support or an implant) represented by the medical image data. That is, in the example of FIG. 3, three second criteria are indicated with the lines 56, 58, 60, each being associated with a different surface type (e.g., a skin surface, a bone surface and a metal surface).

Referring back to FIG. 2, in optional step 28, a second surface model of the second surface is generated based on the second criterion and the medical image data. Step 28 may comprise identifying all pixels or voxels of the medical image data that meet the second criterion and including all these identified pixels or voxels in the second surface model. Alternatively, step 28 may comprise identifying all pixels or voxels of a predefined portion of the medical image data that meet the second criterion and including all these identified pixels or voxels in the second surface model. The predefined portion may be chosen depending on a surface type of the second surface represented by the second surface model. The second surface model may either represent a (e.g., skin or bone) surface of all parts of the patient depicted by the medical image data, or a (e.g., skin or bone) surface of a selection of parts of the patient depicted by the medical image data. Generating the second surface model may comprise rendering the medical image data based on the second criterion. The generated second surface model or the rendered medical image data may then be visualized on the display device 20 (e.g., as a rough surface estimate).

In optional step 30, a second portion of the second surface as modeled by the second (e.g., rough or preliminary) surface model is identified. The identified second portion represents at least one predefined anatomical region of the patient's body. Each of the at least one predefined anatomical region may be a connected or continuous region. One or more (e.g., each) of the at least one predefined anatomical region may be or comprise an anatomical landmark of the patient's body (e.g., a nose tip).

The second portion may be identified based on feature recognition. The second portion may be identified using an anatomical atlas (e.g., by matching the at least one anatomical region as represented by the anatomical atlas to the second surface model). The second portion may be identified by identifying parts of the second surface model that meet predefined geometrical criteria associated with the at least one anatomical region. The predefined geometrical criteria may comprise at least one of a predefined (e.g., minimum, maximum or average) curvature, a predefined (e.g., minimum, maximum or average) width and a predefined (e.g., minimum, maximum or average) height. Other variants for identifying the second portion are also possible. The at least one predefined anatomical region may be associated with the surface type of the second surface.

In step 32, a first portion of the medical image data is identified. The first portion represents at least one predefined anatomical region. One or more (e.g., each) of the at least one predefined anatomical region may be or comprise an anatomical landmark of the patient's body (e.g., a nose tip). The first portion may be identified based on the second portion identified in optional step 30. In case optional step 30 is performed, the first portion may represent the same at least one predefined anatomical region as the second portion. The first portion of the medical image data may consist of or comprise the pixels or voxels associated with the second portion. That is, the second portion may be used to select a set of pixels or voxels of the medical image data to be included in the first portion. In case step 30 is not performed, the first portion may be identified based on feature recognition, using an anatomical atlas and/or by identifying parts (e.g., one or more anatomical landmarks) represented by the medical image data that meet (e.g., the) predefined geometrical criteria associated with the at least one anatomical region. The first portion may be a spatial portion represented by the medical image data, for example a subset of pixels or voxels of the medical image data, which pixels or voxels may represent the at least one predefined anatomical region.

The first portion may be associated with or identified based on the type of the first surface. The first portion may be identified based on a thickness of tissue between a bone of the patient's body and the skin of the patient's body. In case the first surface is a bone surface, the first portion may consist of portions of the patient's body in which the thickness of the tissue between the bone and the skin is less than a predefined thickness (e.g., less than 3 mm, less than 2 mm or less than 1 mm). In case the first surface is a skin surface, the first portion may consist of portions of the patient's body in which the thickness of the tissue between the bone and the skin is more than a predefined thickness (e.g., more than 3 mm, more than 5 mm or more than 10 mm). The first portion of the medical image data may be identified based on two or more second portions of the second surface, each representing a different type (e.g., a bone surface and a skin surface, respectively) of second surface.

In step 34, a first criterion for allocating pixels or voxels of the medical image data to a first surface represented by the medical image data is determined (e.g., only or exclusively) based on the first portion of the medical image data. The first criterion may be specific for the identified first portion. The first criterion may be specific for the medical image data and, thus, for the patient. All pixels or voxels of the first surface fulfil the first criterion. The "first criterion" may also be referred to as final criterion, refined criterion or precise criterion, and the "first surface" may also be referred to as final surface, refined surface or precise surface. The first criterion may comprise a (e.g., threshold) value of pixels or voxels of the medical image data representing a part of the first surface. The value may be representative of a strength of a signal received by the detector 18 of the medical imaging device 12. The first criterion may be or comprise at least one threshold value or a range of values associated with the first surface.

The first criterion may be determined based on a value of at least one pixel or voxel of the first portion of the medical image data, which at least one pixel or voxel may also be part of the second portion. The first criterion may be determined based on values of pixels or voxels of one or more sets (e.g., samples) of pixels or voxels of the medical image data, wherein the pixels or voxels of each set lie along a same straight (e.g., virtual) line associated with the respective set and, optionally, have values within a predefined value range (e.g., associated with the surface type of the first surface). Each line may be referred to as a sampling line or a reading line. The lines of different sets may differ from one another in at least one of position and orientation relative to the patient's body as represented by the medical image data.

Generally speaking, the first criterion may be determined based on the second portion. In particular, the (e.g., each) line may have a predefined spatial relationship to the second surface as modeled by the second surface model, for example a predefined spatial relationship to the second portion. For example, the line may intersect the second portion and/or have a predefined angle relative to at least a part of the second portion (e.g., a predefined angle at the intersection point). The line may intersect the second portion at an intersection point and be orthogonal to the second surface model or the second portion at the intersection point. Alternatively, or in addition, the line may have a predefined angle relative to another line associated with another one of the one or more sets. It is also possible that the line has a predefined distance relative to (e.g., the) another line associated with (e.g., the) another one of the one or more sets. At least one of a pose (e.g., at least one of a position and an orientation) relative to the second portion, a length and an intersection point of the respective line may depend on (e.g., be selected or determined based on) a surface type of the first surface.

Figure 4:
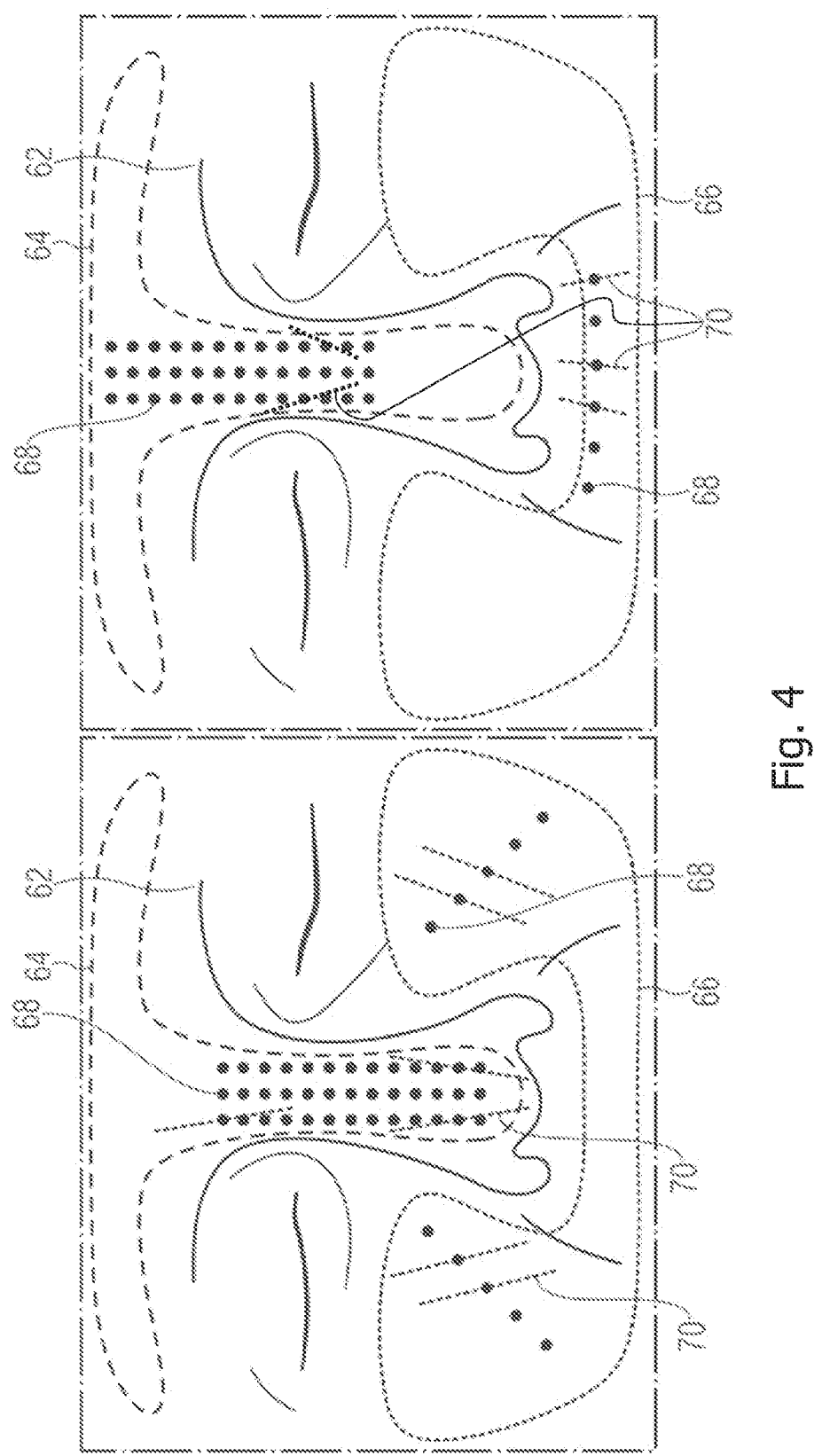
FIG. 4 shows a surface in accordance with the present disclosure.

This approach using sampling lines will now be described with reference to FIG. 4, which shows a visualization of a second (e.g., preliminary or rough) surface model 62 in accordance with the present disclosure. In this example, the medical image data comprises CT image data and all voxels that meet a skin threshold as the second criterion are included in the second surface model. Also indicated in FIG. 4 are two examples of the second portion, namely second portion 64 that represents the patient's nose and forehead as the at least one predefined anatomical region, and second portion 66 that represents the patient's cheeks and philtrum as the at least one predefined anatomical region. The first criterion may thus be determined based on each of the second portions 64, 66 individually. That is, each of the second portions 64, 66 may be used to identify a respective first portion, which may then be used to determine the respective first criterion. It is also possible for the second portion to cover the complete surface of the patient's body as represented by the medical image data and to determine a single first criterion for the overall medical image data.

Also indicated in FIG. 4 are intersection points 68 between the sampling lines 70 and the second surface as represented by the second surface model 62. Note that only a selection of the sampling lines 70 is illustrated here. The intersection points 68 lie within the respective second portion 64, 66. The lines 70 intersecting the respective second portion 64, 66 at the intersection points 68 are normal or orthogonal to the second surface as represented by the second surface model 62 at the respective intersection points 68. Neighboring intersection points 68 of a group of intersection points 68 within a same second portion 64 or 66 are spaced apart from another by a predefined distance.

The difference between the left illustration of FIG. 4 and the right illustration of FIG. 4 is that different intersection points 68 and different lines 70 are shown. For example, the intersection points 68 and the lines 70 of the left illustration may be used to determine the first criterion for the first surface if the first surface is a skin surface. On the other hand, the intersection points 68 and the lines 70 of the right illustration may be used to determine the first criterion for the first surface if the first surface is a bone surface.

Generally speaking, the sampling lines 70 allow for a sampling of pixels or voxels of the medical image data for determining the first criterion. Each of the lines 70 may be used to determine an estimate of the first criterion. All estimates of the lines 70 intersecting intersection points 68 of the same second portion 64 or 66 may then be used to determine the first criterion for this second portion. For example, all estimates determined based on the lines 70 intersecting the intersection points 68 lying within the second portion 64 may be averaged to determine the first criterion for the first surface. The first surface may be associated with the respective second portion 64, 66. One may say that the second portion 64 of the rough second surface model 62 may be used to determine the first criterion, which first criterion may then be used to refine the model of the second portion 64 by generating the first surface model thereof. Put differently, the preliminary second surface model of a particular second portion may be determined using the second criterion, and the preliminary second surface model may then be used to determine a more accurate criterion as the first criterion, thereby allowing the determination of a precise first surface model (e.g., of the first portion, the second portion or the overall patient surface).

The first criterion may be determined in step 34 of FIG. 2 based on a trained machine learning model and/or a gradient analysis of pixels or voxels of at least one of the sets of pixels or voxels. One example of this approach will now be described with reference to FIG. 5.

Figure 5:
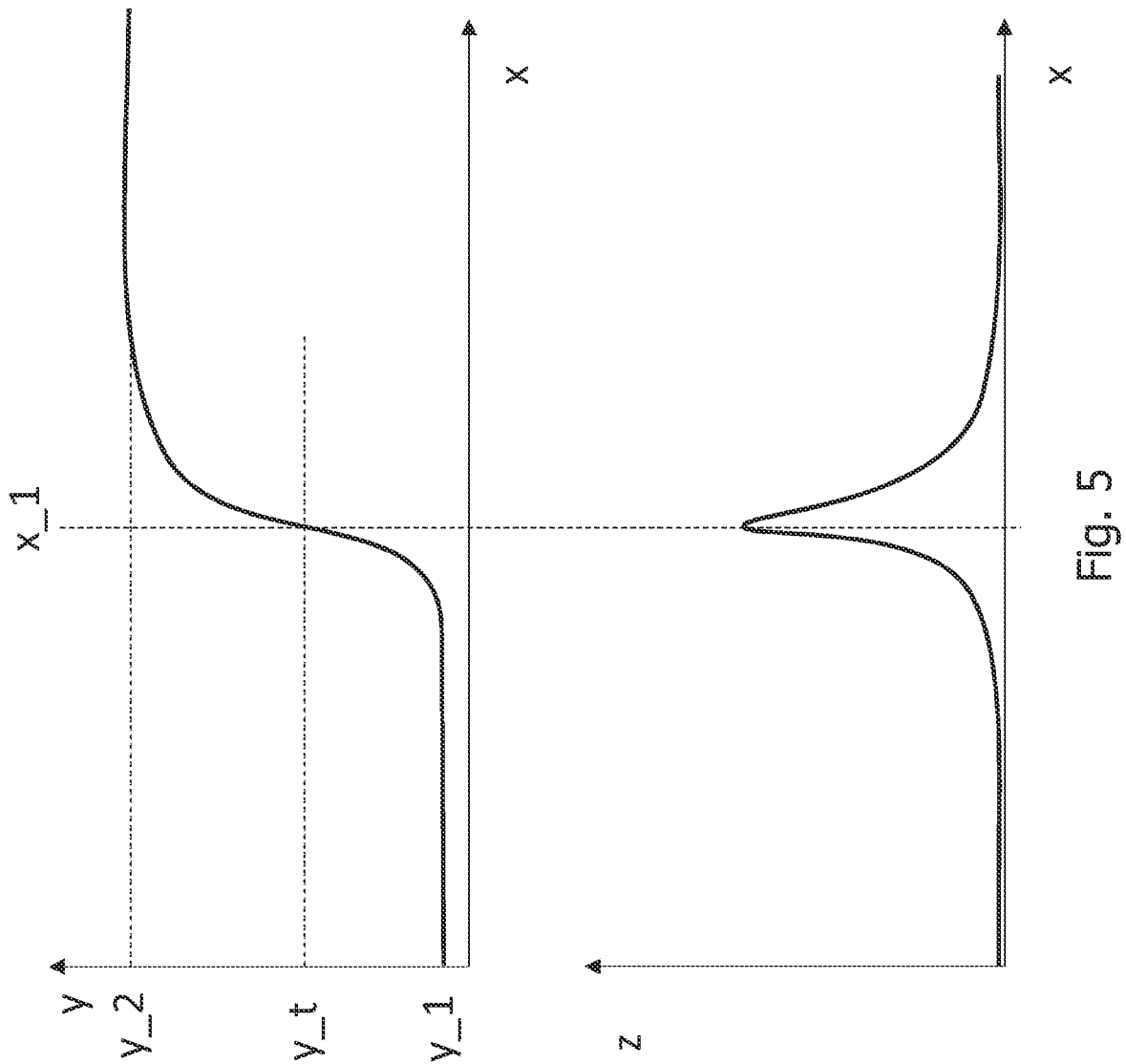
FIG. 5 shows exemplary values and a gradient of pixels or voxels in accordance with the present disclosure.

FIG. 5 shows exemplary values and a gradient of pixels or voxels in accordance with the present disclosure. The x-axis designates positions along the length of one exemplary sampling line 70. The y-axis designates a (e.g., intensity or Hounsfield) value of the respective voxels on the line 70. The z-axis designates the gradient size of the voxel values along the length of the line 70.

In this example, the voxel values change from a lower range y1 to a higher range y2 along the length of the line 70. The maximum rate of change along the length of the line 70 occurs at the position x1 and corresponds to the local maximum of the gradient values as apparent from the curve in the bottom illustration of FIG. 5. The voxel value y_t may be used as the estimate of the first criterion associated with this particular line 70. The value y_t may be determined by analyzing the gradient values as illustrated in the bottom illustration of FIG. 5 to detect local and/or global maxima. In case multiple maxima are detected, the respective values y_t may be compared with predefined ranges of voxel values to select one of the values y_t as the estimate of the first criterion. These predefined ranges may be determined or defined by the second criterion. For example, each surface type may be associated with a different second criterion and each different second criterion may be used to assign different y_t values to the different surface types. Furthermore, if more than one line 70 is used, all estimates for a particular surface type may be averaged to determine the first criterion for this surface type. Alternatively, y_t of a single line 70 may be used as the first criterion.

Instead of detecting the maximum of the gradient values using the above-described gradient analysis, the voxel values of the voxels lying on the line 70 may be used as an input for a trained machine learning model. The surface type of the first and/or second surface may be used as an additional input. The trained machine learning model may then output the first criterion.

The first criterion may allow for an accurate and precise detection of the first surface based on the medical image data.

Referring back to FIG. 2, in optional step 36, based on the first criterion and the medical image data, a first surface model of the first surface is generated. Step 36 may comprise identifying all pixels or voxels of the medical image data that meet the first criterion and including all these identified pixels or voxels in the first surface model. Alternatively, step 36 may comprise identifying all pixels or voxels of a (e.g., the) predefined portion or of the first portion of the medical image data that meet the first criterion and including all these identified pixels or voxels in the first surface model. The first surface model may either represent a (e.g., skin or bone) surface of all parts of the patient depicted by the medical image data, or a (e.g., skin or bone) surface of a selection of parts of the patient depicted by the medical image data. Generating the first surface model may comprise rendering (e.g., the first portion of) the medical image data based on the first criterion. The generated first surface model or the rendered medical image data may then be visualized on the display device 20 (e.g., as a refined surface estimate).

Multiple first portions of the medical image data may be identified and multiple first criteria may be determined based on the multiple first portions for allocating pixels or voxels of the medical image data to respective first surfaces represented by the medical image data. This may allow for a determination of a plurality of refined surface estimates, each based on a different one of the first criteria (e.g., a plurality of first surface models for different portions of the patient's body). The first surface model may be representative of a combination of all these respective first surfaces, or multiple first surface models may be provided, each representative of a respective first surface. Alternatively, the multiple first criteria may be combined (e.g., averaged) to determine a single first criterion for allocating pixels or voxels of the medical image data to the (e.g., combined) first surface (e.g., including the predefined anatomical regions associated with all first portions used to determine the multiple first criteria).

Each surface (e.g., the first surface and the second surface) may be of a surface type. The surface type may be one of (i) a bone surface of the patient's body, (ii) a skin surface of the patient's body, or (iii) a (e.g., metal) surface of a clinical object. The clinical object may be a head support, an eye protection, a patient bed, a head fixation device, a component of the medical imaging device 12 or an implant inside or attached to the patient's body. The first surface and the second surface may be of the same surface type or of a different surface type. The method, at least step 34, may be performed multiple times, each time for a different surface type of the first surface.

As indicated in FIG. 2, the method may comprise optional step 38. Step 38 may be performed at some point after step 24 (e.g., before any one of steps 26-36). In step 38, the medical image data is adapted. The adapted medical image data may then be used instead of the medical image data in one or more (e.g., all) of the subsequent method steps.

It is noted that in one variant, step 38 may be performed without one or more (e.g., without any) of steps 26-36. The present disclosure thus provides for a method comprising only steps 24 and 38, and optionally further comprising one or more of the steps 26-36. This method may be performed by the processor 6.

Adapting the medical image data may comprise at least one adaption selected from: (i) excluding imaging artifacts from the medical image data (step 40 in FIG. 2); (ii) excluding one or more clinical objects represented by the medical image data (step 42 in FIG. 2); and (iii) changing a spatial orientation of the medical image data (step 44 in FIG. 2). Adapting the medical image data may comprise (i) performing, iteratively, two or more of the at least one adaption to gradually adapt the medical image data, and/or (ii) performing, iteratively, one of the at least one adaption multiple times to gradually adapt the medical image data.

These adaptions will now be described in detail with reference to FIGS. 6 to 8.

Figure 6:
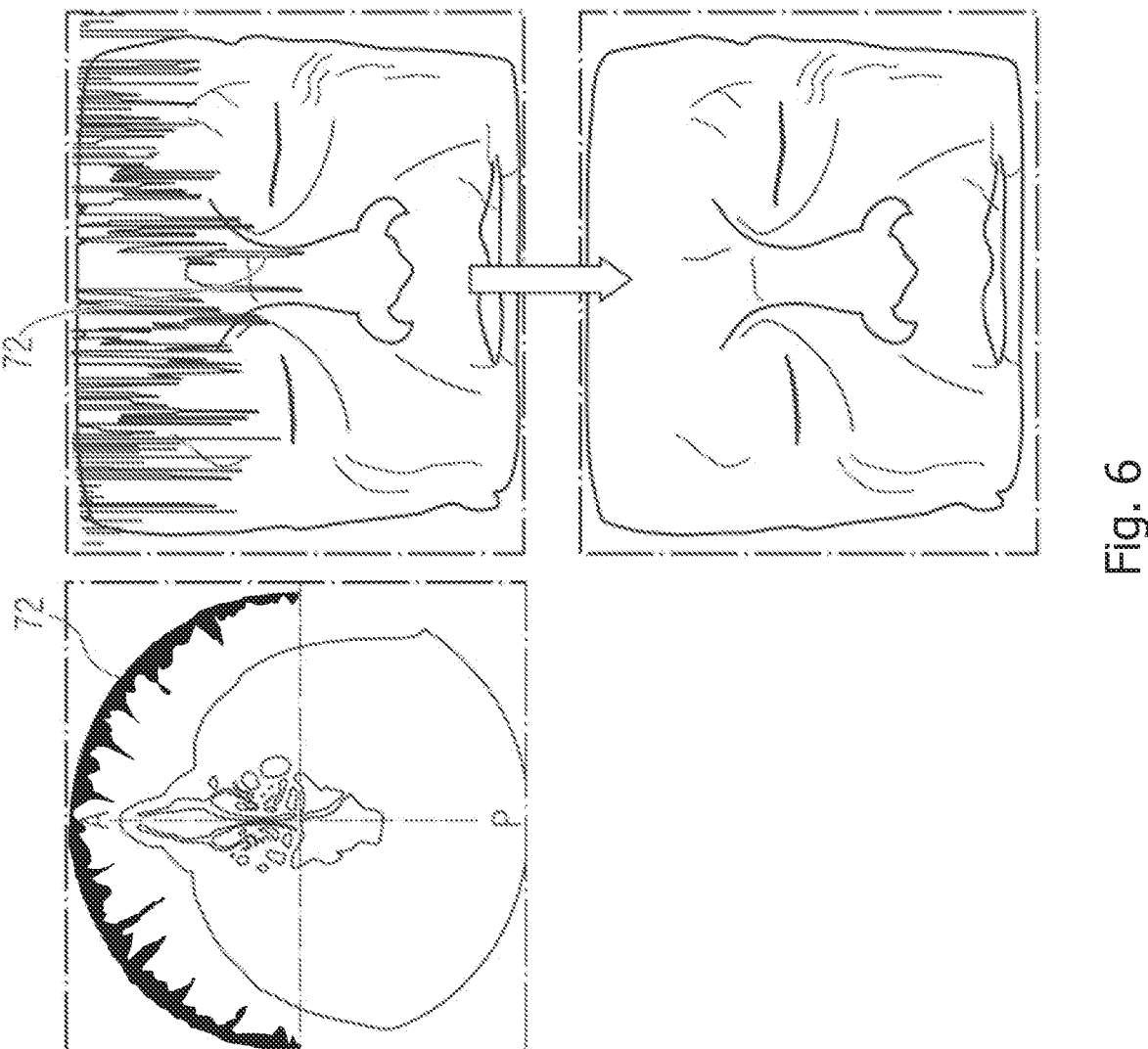
FIG. 6 illustrates a removal of imaging artifacts in accordance with the present disclosure.

FIG. 6 illustrates a removal of imaging artifacts in accordance with the present disclosure, for example as performed in step 40. In this example, the medical image data comprises cone beam CT image data of a patient's head. The top left illustration shows a visualization of a cross section of the CT image data in the transverse plane. The arrow in this illustration points to some typical imaging artifacts 72 of cone beam CT scanners. The top right illustration shows a rendering of the skin surface of the patient's head based on the CT image data. The imaging artifacts 72 are clearly visible as vertical lines in the upper image portion. The imaging artifacts 72 may be removed by masking out portions of the CT image data, for example all voxels within a predefined distance (e.g., 10 mm) from the outer image boundary. The mask for masking out portions of the CT image data may be cylindrical or spherical. The imaging artifacts may be detected using a (e.g., adapted) Hough transformation applied to the volumetric image data, and the detected artifacts may then be excluded. Alternatively, or in addition, a filter may be applied to the medical image data or a trained machine learning model may be used to exclude the imaging artifacts 72. By removing these imaging artifacts 72, the medical image data can be advantageously adapted, as apparent from the bottom illustration. This allows a more reliable detection of the skin surface, for example.

Figure 7:
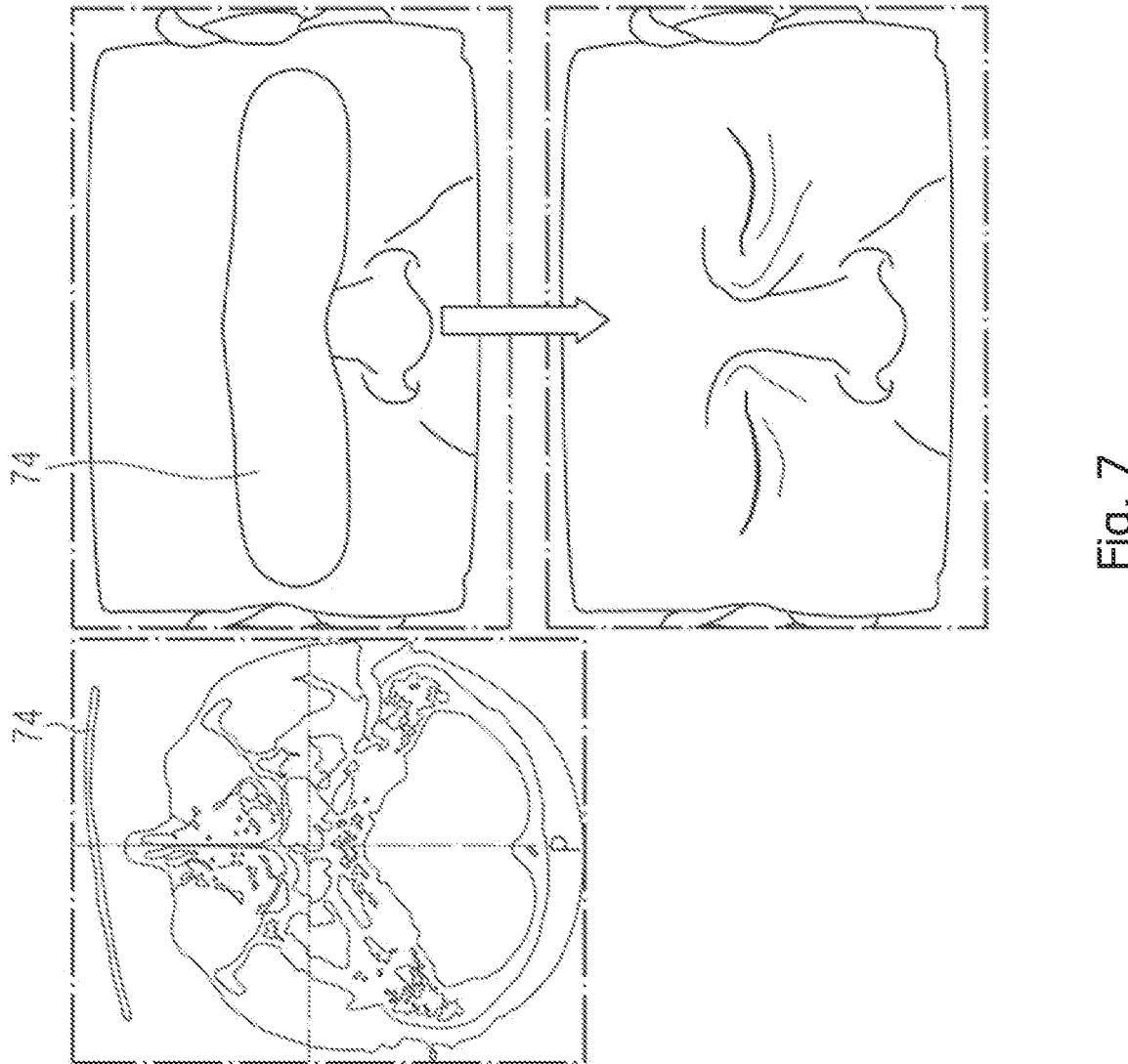
FIG. 7 illustrates an exclusion of an eye protection in accordance with the present disclosure.

FIG. 7 illustrates an exclusion of an eye protection 74 in accordance with the present disclosure, for example as performed in step 42. In this example, the medical image data comprises CT image data of a patient's head. The top left illustration shows a visualization of a cross section of the CT image data in the transverse plane. At the top of this illustration, a bright horizontal element above the patient's nose can be seen. This element is the eye protection 74 made of metal and placed on the patient during the acquisition of the CT scan to reduce irradiation of the patient's eyes. The eye protection 74 can be detected by identifying voxels having values that meet a (e.g., first or second) criterion associated with a metal surface. Alternatively, (e.g., machine-learning based) feature or object recognition techniques may be used for detecting the eye protection 74. By removing the eye protection 74 from the medical image data (e.g., by masking out all pixels or voxels that exceed a metal threshold associated with the eye protection 74), the medical image data can be advantageously adapted as shown in the bottom illustration. This reduces ambiguity regarding which surface to interpret as being part of the patient, and allows a more reliable detection of the skin surface, for example.

Figure 8:
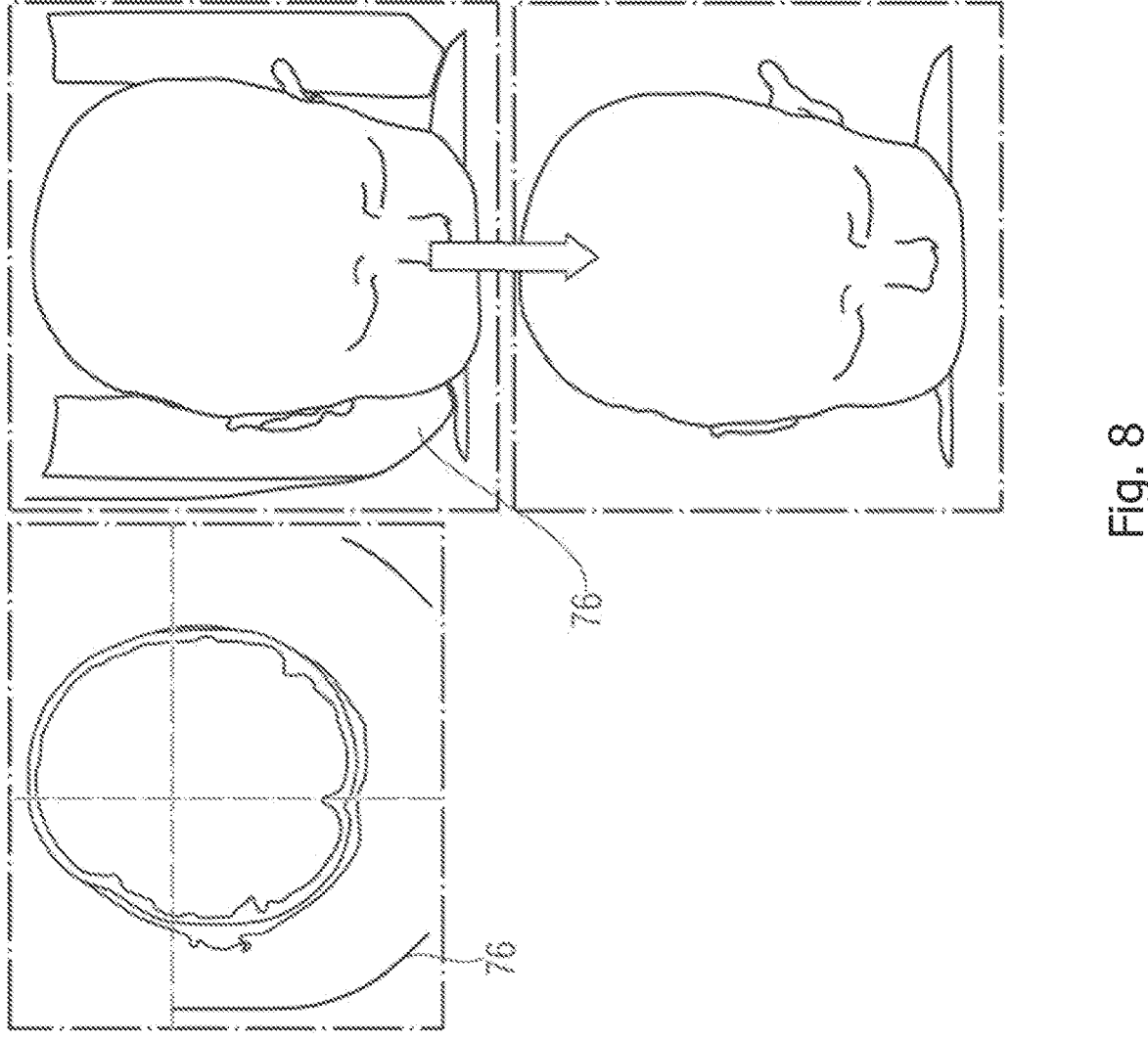
FIG. 8 illustrates an exclusion of a head support in accordance with the present disclosure.

FIG. 8 illustrates an exclusion of a head support 76 in accordance with the present disclosure, for example as performed in step 42. In this example, the medical image data comprises CT image data of a patient's head. The top left illustration shows a visualization of a cross section of the CT image data in the transverse plane. At the bottom of this illustration, a bright U-shaped element below the patient's head can be seen. This element is the head support 76 (e.g., made of plastic) and placed under the patient during the acquisition of the CT scan to hold the patient's head in a wanted pose. The head support 76 can be detected by identifying voxels having values that meet a (e.g., first or second) criterion associated with a plastic surface. Alternatively, (e.g., machine-learning based) feature or object recognition techniques may be used for detecting the head support 76. As another example, the head may be detected based on the medical image data, for example by determining the second surface model of the skin surface. Any objects exterior to the skin surface as represented by the skin model may be identified as clinical objects to be excluded. By removing the head support 76 from the medical image data, the medical image data can be advantageously adapted, as shown in the bottom illustration. This reduces ambiguity regarding which surface to interpret as being part of the patient, and allows a more reliable detection of the skin surface, for example.

Although the examples of FIGS. 6 to 8 are shown based on medical image data of different patients, it is to be understood that the removal of imaging artifacts, the exclusion of the eye protection and the exclusion of the head support may all be performed for the same medical image data (e.g., for CT image data of one and the same patient).

Figure 9:
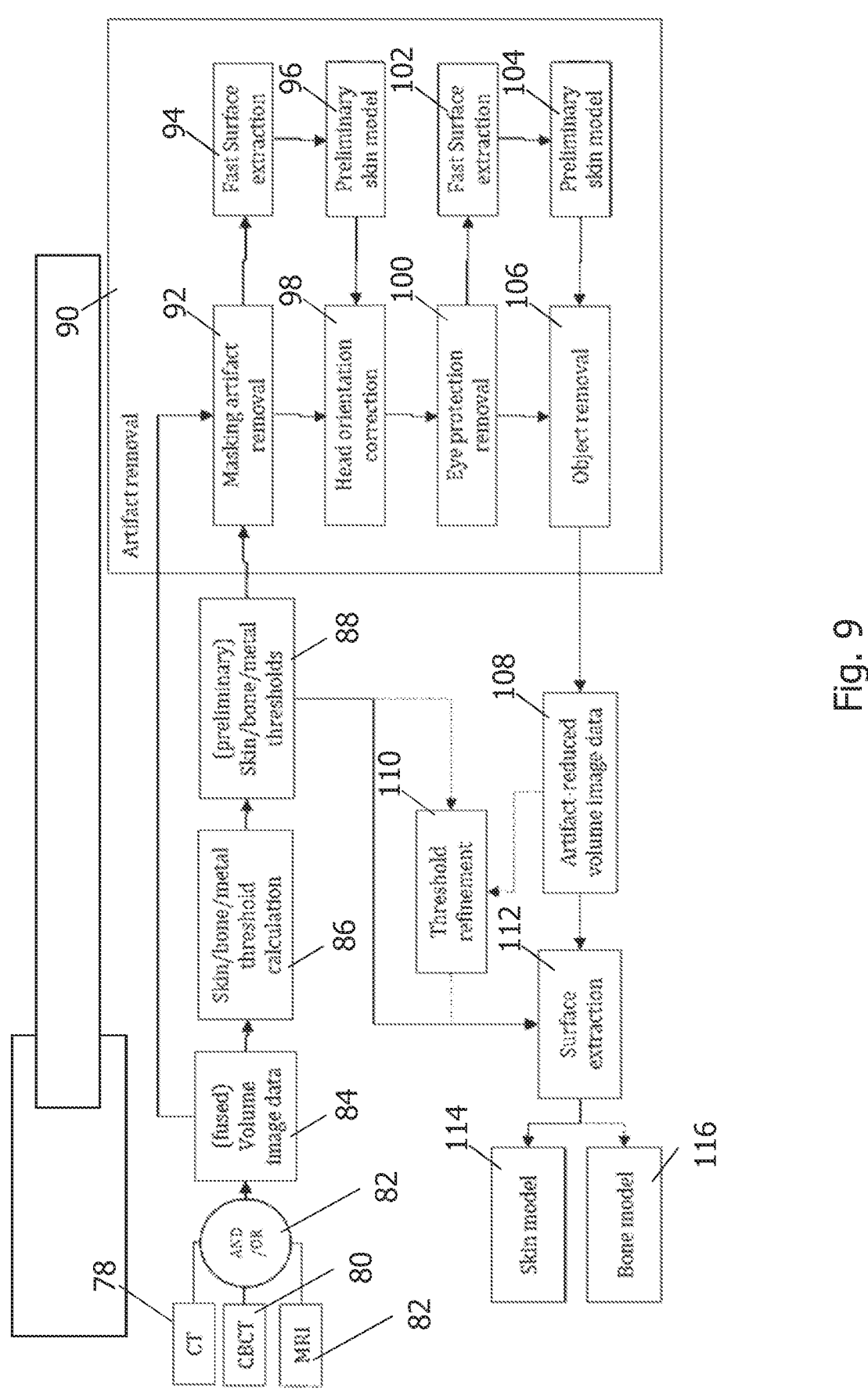
FIG. 9 illustrates a flow chart of a method in accordance with the present disclosure.

FIG. 9 illustrates a flow chart of a method in accordance with the present disclosure. As mentioned above and as indicated in FIG. 9, the medical image data may comprise CT image data 78, cone beam CT image data (CBCT) 80 and/or MR image data (MRI) 82. These volumetric image data may be fused or registered to one another in a step 82 to obtain (e.g., fused or registered) volume image data 84. In one variant, the image data 84 corresponds to the medical image data. The "preliminary Skin/bone/metal thresholds" 86 may correspond to the second criteria for the surface types skin, bone and metal. These thresholds may be determined based on the medical image data as described herein with reference to step 26 (see also the description of FIG. 3).

The block "Artifact Removal" 90 may correspond to step 38 described herein. The bock "Masking artifact removal" 92 may correspond to the exclusion of imaging artifacts as described herein above. The block "Head orientation correction" 98 may correspond to the change of the spatial orientation of the medical image data as described herein above. The block "Eye protection removal" 100 may correspond to the exclusion of the eye protection (e.g., 74) as a clinical object, as described herein above. The block "Object removal" 106 may comprise the exclusion of another clinical object such as the head support 76. As indicated in FIG. 9, the artifact removal technique may be performed iteratively by adapting the medical image data 84 and using the adapted medical image data during a subsequent adaption. This may gradually adapt or improve the medical image data step by step. As a final result of block 90, artifact-reduced volume image data 108 is obtained.

As indicated in FIG. 9, the head orientation correction step 98 may be performed based on a preliminary skin model 96 (e.g., the second surface model), obtained in step 94 using a fast surface extraction (e.g., using one or more of the (e.g., preliminary) skin/bone/metal threshold(s) 88). For example, the preliminary skin model 96 can be used to detect a pose of the patient's head as represented by the image data 84 and the spatial orientation of the image data 84 may be corrected to adjust the detected pose to a predefined pose. Furthermore, the object removal step 106 may be performed based on another preliminary skin model 104 (e.g., the second surface model) obtained in step 102 using a fast surface extraction (e.g., applying one or more of the (e.g., preliminary) skin/bone/metal threshold(s) 88 to the image data as adapted in steps 92-100). For example, the preliminary skin model 104 may be used to remove any objects exterior to a skin surface of the patient's body form the medical image data as adapted in steps 92-100. As indicated in block 90, as an alternative, the steps 94, 96 and/or the steps 102 and 104 may be omitted.

The block "Threshold refinement" 110 may correspond to the determination of the first criterion. As indicated in FIG. 9, this first criterion may be used in the block "Surface extraction" 112 (e.g., to generate the first surface model of the skin surface as the "Skin model" 114 or of the bone surface as the "Bone model" 116).

The block "Artifact removal" 90 in FIG. 9 may be performed without the subsequent steps (e.g., without blocks 110-114). In this case, the outcome of the method is the adapted medical image data or "artifact-reduced volume image data" 108, which may then be used as desired (e.g., for generating the first surface model, performing a surface-based image registration or generating a visualization of the adapted medical image data to be displayed on the display unit 20).

The present disclosure also provides for a computer program comprising instructions which, when executed on the processor 6, cause the processor 6 to carry out the method(s) described herein. A carrier (e.g., the memory 8) containing the computer program may also be provided.

The machine learning models described herein may comprise (e.g., deep or convolutional) neural networks. Such networks may be trained based on labeled training data using supervised learning, for example.

Various modifications of the techniques described herein are possible. For example, step 38 may be performed between steps 24 and 26, between steps 30-32 or between steps 34 and 36. The medical image data may comprise two-dimensional image data and the surfaces and surface models may correspond to (e.g., continuous) lines, but the medical image data may also comprise three-dimensional (e.g., volumetric) image data and the surfaces and surface models may be defined in three dimensions.

The technique described herein may improve medical image data by subjecting it to image adaption. Artifacts and unwanted clinical objects such as eye protections, head supports or implants may be removed and the orientation of the image data may be corrected. This may allow for a more reliable and accurate detection of a skin or bone surface of the patient's body. Furthermore, instead of using a single, predefined threshold for identifying a (e.g., skin or bone) surface based on the medical image data of the patient's body, the first criterion is determined based on the identified first portion. The first portion represents at least one predefined anatomical element (e.g., the patient's nose). One may thus say that the first criterion, usable for detecting the skin or bone surface, is locally defined and patient specific. This also enables a more reliable and accurate detection of the skin or bone surface of the patient's body. The details described herein above are particularly useful and advantageous. For example, it has been found that an improved surface detection is possible when determining the first criterion using one or more sampling lines as described herein. Further modifications and advantages may become apparent to those skilled in the art.

The invention claimed is:

1. A method for processing medical image data of a patient's body, the method comprising:
   (a) obtaining medical image data of a patient's body;
   (b) identifying a first portion of the medical image data that represents at least one predefined anatomical region of the patient's body;
   (c) determining, based on the first portion of the medical image data, a first criterion for allocating pixels or voxels of the medical image data to a first surface represented by the medical image data;

(d) obtaining a second criterion for allocating pixels or voxels of the medical image data to a second surface represented by the medical image data, the second criterion determined based on the medical image data and on at least one of:

(i) a histogram analysis of values of pixels or voxels of the medical image data; and (ii) a trained machine learning model (e) generating, based on the second criterion and the medical image data, a second surface model of the second surface; and (f) identifying a second portion of the second surface as modeled by the second surface model that represents the at least one predefined anatomical region, wherein the first criterion is determined based on values of pixels or voxels of one or more sets of pixels or voxels of the medical image data, and the pixels or voxels of each set lie along a same straight line associated with the respective set, wherein the line has a predefined spatial relationship to the second surface as modeled by the second surface model.

2. The method of claim 1, wherein the first criterion comprises a value of pixels or voxels of the medical image data representing a part of the first surface.

3. The method of claim 2, wherein the value is representative of a strength of a signal received by a detector of a medical imaging device.

4. The method of claim 1, further comprising generating, based on the first criterion and the medical image data, a first surface model of the first surface.

5. The method of claim 1, wherein the second criterion is predefined, user-defined or determined based on the medical image data.

6. The method of claim 5, wherein at least one of the following conditions is fulfilled:

(i) the first portion of the medical image data is identified based on the second portion; and (ii) the first criterion is determined based on the second portion.

7. The method of claim 1, wherein at least one of the following conditions is fulfilled:

the line intersects the second portion;

the line has a predefined angle relative to at least a part of the second portion;

the line intersects the second portion at an intersection point and is orthogonal to the second portion at the intersection point;

the line has a predefined angle relative to another line associated with another one of the one or more sets; and the line has a predefined distance relative to another line associated with another one of the one or more sets.

8. The method of claim 1, wherein the first criterion is determined based on a trained machine learning model and/or a gradient analysis of pixels or voxels of at least one of the sets.

9. The method of claim 1, wherein multiple first portions of the medical image data are identified and wherein multiple first criteria are determined based on the multiple first portions for allocating pixels or voxels of the medical image data to respective first surfaces represented by the medical image data.

10. The method of claim 1, further comprising:

adapting the medical image data before performing at least one of the method steps, wherein, during the at least one method step, the adapted medical image data is used instead of the medical image data, wherein adapting the medical image data comprises at least one adaption selected from:

(i) excluding imaging artifacts from the medical image data;

(ii) excluding one or more clinical objects represented by the medical image data; and (iii) changing a spatial orientation of the medical image data.

11. The method of claim 10, wherein the step of adapting the medical image data comprises:

(i) performing, iteratively, two or more of the at least one adaption, or (ii) performing, iteratively, one of the at least one adaption multiple times, to gradually adapt the medical image data.

12. The method of claim 1, wherein each surface is of a surface type, and wherein the surface type is one of:

(i) a bone surface of the patient's body, (ii) a skin surface of the patient's body, or (iii) a surface of a clinical object.

13. The method of claim 12, wherein at least the step (c) is performed multiple times, each time for a different surface type of the first surface.

14. A computing system comprising at least one processor configured to:

(i) obtain medical image data of a patient's body;

(ii) identify a first portion of the medical image data that represents at least one predefined anatomical region of the patient's body;

(iii) determine, based on the first portion of the medical image data, a first criterion for allocating pixels or voxels of the medical image data to a first surface represented by the medical image data;

(iv) obtain a second criterion for allocating pixels or voxels of the medical image data to a second surface represented by the medical image data, the second criterion determined based on the medical image data and on at least one of:

(a) a histogram analysis of values of pixels or voxels of the medical image data; and (b) a trained machine learning model (v) generate, based on the second criterion and the medical image data, a second surface model of the second surface; and (vi) identify a second portion of the second surface as modeled by the second surface model that represents the at least one predefined anatomical region, wherein the first criterion is determined based on values of pixels or voxels of one or more sets of pixels or voxels of the medical image data, and the pixels or voxels of each set lie along a same straight line associated with the respective set, wherein the line has a predefined spatial relationship to the second surface as modeled by the second surface model.

15. A computer readable storage medium storing a computer program comprising instructions which, when executed on at least one processor, cause the at least one processor to:

(i) obtain medical image data of a patient's body;

(ii) identify a first portion of the medical image data that represents at least one predefined anatomical region of the patient's body;

(iii) determine, based on the first portion of the medical image data, a first criterion for allocating pixels or voxels of the medical image data to a first surface represented by the medical image data (iv) obtain a second criterion for allocating pixels or voxels of the medical image data to a second surface represented by the medical image data, the second criterion determined based on the medical image data and on at least one of:
    (a) a histogram analysis of values of pixels or voxels of the medical image data;
    (b) a trained machine learning model and (v) generate, based on the second criterion and the medical image data, a second surface model of the second surface; and (vi) identify a second portion of the second surface as modeled by the second surface model that represents the at least one predefined anatomical region, wherein the first criterion is determined based on values of pixels or voxels of one or more sets of pixels or voxels of the medical image data, and the pixels or voxels of each set lie along a same straight line associated with the respective set, wherein the line has a predefined spatial relationship to the second surface as modeled by the second surface model.

16. The method of claim 13, further comprising:

adapting the medical image data after performing at least step (c), wherein adapting the medical image data comprises excluding one or more clinical objects based on the surface type.

\* \* \* \* \*